Figure 1:
Figure 2:
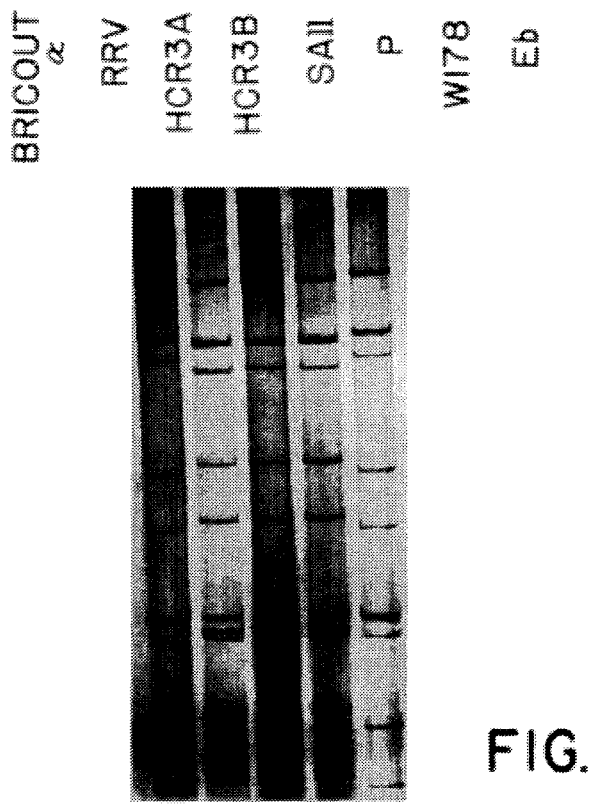

US005610049A

United States Patent [19]
Clark

[11] Patent Number: 5,610,049
[45] Date of Patent: Mar. 11, 1997

[54] HUMAN ROTAVIRUS HCR3A AND METHOD OF GROWING SAID ROTAVIRUS

[75] Inventor: H. Fred Clark, Philadelphia, Pa.

[73] Assignee: The Wistar Institute of Anatomy and Biology, Philadelphia, Pa.

[21] Appl. No.: 694,968

[22] Filed: May 1, 1991

[51] Int. Cl.$^6$ .............................. C12N 7/00; C12N 7/02; C12N 7/08; A61K 39/15
[52] U.S. Cl. ..................... 435/235.1; 435/237; 435/239; 435/236; 424/215.1
[58] Field of Search .................................. 424/89, 215.1; 435/235.1, 239, 236, 237

[56] References Cited

U.S. PATENT DOCUMENTS

| | | | |
|---|---|---|---|
| 3,293,129 | 12/1966 | Baker . | |
| 4,190,645 | 2/1980 | Almeida | 435/236 |
| 4,205,131 | 5/1980 | Almeida | 435/235.1 |
| 4,341,763 | 7/1982 | Zygraich | 424/215.1 |
| 4,341,870 | 7/1982 | Wyatt et al. | 435/237 |
| 4,571,385 | 2/1986 | Greenberg et al. | 435/172.3 |
| 4,624,850 | 11/1986 | Albert et al. | 424/215.1 |
| 4,636,385 | 1/1987 | Plotkin et al. | 424/215.1 |
| 4,704,275 | 11/1987 | Wyatt et al. | 424/215.1 |
| 4,751,080 | 6/1988 | Wyatt et al. | 424/205.1 |
| 4,853,333 | 8/1989 | Hsiao et al. | 435/254.21 |
| 4,861,864 | 8/1989 | Atkinson et al. | 530/324 |
| 4,927,628 | 5/1990 | Chanock et al. | 424/205.1 |

FOREIGN PATENT DOCUMENTS

| | | |
|---|---|---|
| 0130906 | 1/1985 | European Pat. Off. . |
| 0152295 | 8/1985 | European Pat. Off. . |
| 0192404 | 8/1986 | European Pat. Off. . |
| 0235391 | 9/1987 | European Pat. Off. . |
| 0323708 | 7/1989 | European Pat. Off. . |
| 1276218 | 6/1972 | United Kingdom . |
| 2009768 | 6/1979 | United Kingdom . |
| WO92/08786 | 5/1992 | WIPO . |

OTHER PUBLICATIONS

Li et al. Virology 196:825–830 1993.
Hayflick et al. Am.J. Hyg 75:240–58 1962.
Kitaoka, S. et al. (1987) J. Medical Virology 23:351–357.
Absudy, Y. et al. (88) J. Med. Virol. 25:351–359.
Nakagomi, O. et al. (87) J. Clin. Microbiol. 25:1159–1164.
Nakagomi, O. et al. (88) Ann. Inst. Pasteur/Virol. T39:295–300.
Gerna, G. et al. (90) J. Clin. Microbiol. 28:1342–1347.
G. Gerna et al, Biol. Abstract No. 90046794 and *J. Clin. Microbiol.*, 28(6):1342–1347 (1990).
O. Nakagomi et al, Biol. Abstract No. 84057426 and *J. Clin. Microbiol.*, 25(7):1159–1164 (1987).
R. Ward et al, Biol. Abstract No. 87012291 and *J. Virol.*, 62(11):4358–4361 (1988).
R. S. Daum et al, "New Vaccines Against Rotavirus Gastroenteritis," *Advances in Pediatric Infectious Diseases*, vol. 6, pp. 1–57 (1991) [Daum I].
J. A. Walsh et al, "Special Article, Selective Primary Health Care, An Interim Strategy for Disease Control in Developing Countries", *New Eng. J. Med.*, 301(18):967–974 (1979).

I. deZoysa et al, "Interventions for the Control of Diarrhoeal Diseases Among Young Children: Rotavirus and Cholera Immunization", *Bull WHO*, 63(3):569–583 (1985).
M–S. Ho et al, "Morbidity and Mortality Associated with Rotavirus Diarrhea in the U.S.", 27th Interscience Conf. Antimicrobiol Agents Chemotherapy, p. 2 (1987).
M. K. Estes et al, "Antigenic Structure of Rotaviruses", *Immunochemistry of Viruses, Elsevier, Amsterdam*, pp. 389–405 (1985) [Estes I].
R. G. Wyatt et al, "Definition of Human Rotavirus Serotypes by Plaque Reduction Assay", *Infect. and Immun.*, 37(1):110–115 (1982).
S. Matsuno et al, "A Candidate for a New Serotype of Human Rotavirus", *J. Virol.*, 54(2):623–624 (1985) [Matsuno I].
A. R. Kalica et al, "Identification of the Rotaviral Gene that Codes for Hemagglutination and Protease–Enhanced Plaque Formation", *Virol.*, 125:194–205 (1983) [Kalica I].
H. B. Greenberg et al, "Rescue and Serotypic Characterization of Noncultivable Human Rotavirus by Gene Reassortment", *Infec. and Immunol.*, 37(1):104–109 (1982) [Greenberg I].
M. K. Estes et al, "Molecular Biology and Immunology of Rotavirus Infections", *Immunol. Invest.*, 18(1–4)571–581 (1989) [Estes II].
M. Liu et al, "Identification of the Simian Rotavirus SA11 Genome Segment 3 Product", *Virol.*, 163:26–32 (1988).
L. Bell et al, "Gastroenteritis Caused by Human Rotaviruses (Serotype Three) in a Suckling Mouse Model", *Proc. Soc. Exp. Biol. and Med.*, 184:127–132 (1987).
P. A. Offit et al, "Rotavirus–Specific Cytotoxic T Lymphocyte Response of Mice after Oral Inoculation with Candidate Rotavirus Vaccine Strains RRV or WC3", *J. Infect. Dis.*, 160(5):783–788 (1989) [Offit V].
M. K. Estes, "Rotaviruses and Their Replication", Ch. 48 in *Virology*, 2d ed., pp. 1329–1352, ed. by Fields, Knipe et al, New York (1990) [Estes III].
A. Z. Kapikian et al, "Rotaviruses" Ch. 49 in *Virology*, 2d ed., pp. 1353–1363, ed. Field, Knipe et al, New York (1990) [Kapikian III].
S. Chiba et al, "Protective Effect of Naturally Acquired Homotypic and Heterotypic Rotavirus Antibodies", *The Lancet*, 130:417–421 (1986).
Biological Abstracts, Abstract No. 87033161, T. Urasawa et al, "Preparation of a Human Rotavirus Reassortant with Dual Serotype Specificity vp3 of Serotype 4 and vp7 of Serotype 3", *Sapporo Igaku Zasshi*, 57(4):373–378 (1988).

(List continued on next page.)

*Primary Examiner*—Anthony C. Caputa
*Attorney, Agent, or Firm*—Howson and Howson

[57] ABSTRACT

The present invention refers generally to a novel human cytopathic rotavirus of serotype 3 (HCR3A) and to its use as a vehicle for the expression of human rotavirus genes. The invention also relates to novel rotavirus reassortants, vaccines employing the novel rotavirus and its reassortants and methods for their preparation and administration.

2 Claims, 1 Drawing Sheet

OTHER PUBLICATIONS

Biological Abstracts, Abstract No. 87012291, R. L. Ward et al, "Phenotypic Mixing During Coinfection of Cells with Two Strains of Human Rotavirus", *J. Virol.*, 62(11):4358–4361 (1988).

O. Nakagomi et al, "Nucleotide Sequence Comparison of the VP8* Gene of Rotaviruses Possessing the AU–1 Gene 4 Allele", *J. Gen. Virol.*, 74:1709–1713 (1993).

K. Dolan et al, "Epidemiology of Rotavirus Electropherotypes Determined by a Simplified Diagnostic Technique with RNA Analysis", *J. Clin. Microbiol.*, 21(5):753–758 (1985).

Elizabeth A. Wenske et al, J. Virol., 56(2):613–616 (1985).

Harry B. Greenberg et al, Proc. Natl. Acad. Sci. USA, 78(1):420–424 (1981).

Richard L. Ward et al, J. Virol., 64(7):3219–3225 (1990).

Irene Perez–Schael et al, J. Clin. Microbiol., 28(3):553–558 (1990).

Osamu Nakagomi et al, J. Med. Virol., 28:163–168 (1989).

H F. Clark et al, J. Clin. Microbiol., 25(9):1757–1762 (1987) [Clark I].

H F. Clark et al, Amer. J. Dis. Child., 140:350–356 (1986) [Clark II].

H F. Clark, Rotavirus Vaccines, in Plotkin S.A., Mortinur E.A., eds. Vaccines, Philadelphia, W.B. Saunders, pp. 517–525 (1988) [Clark III].

H F. Clark, Approaches to Immune Protection Against Rotavirus Diarrhea of Infants, Immunization Monitor, 3:3 (1989) [Clark IV].

H F. Clark et al, Ped. Infect. Dis., 4(6):626–631 (1985) [Clark V].

H F. Clark et al, J. Infect. Dis., 161:1099–1104 (1990) [Clark VI].

H F. Clark et al, "A Presumptive New Serotype of Human Rotavirus", 1986 ASM Annual Meeting, Washington, DC, Abstract, (1986) [Clark VII].

H F. Clark, Seminars Ped. Infect. Dis., 2(3):202–206 (1991) [Clark VIII].

P. Offit et al, J. Virol., 57:376–378 (1986) [Offit I].

P. A. Offit et al, J. Virol., 60(2):491–496 (1986) [Offit II].

P. A. Offit et al, J. Virol., 57:46–49 (1986) [Offit III].

P. Offit et al, J. Infect. Dis., 152(6):1152–1158 (1985) [Offit IV].

K. Midthun et al, J. Clin. Microbiol., 24(5):822–826 (1986) [Midthun I].

K. Midthun et al, J. Virol., 53(3):949–954 (1985) [Midthun II].

Y. Hoshino et al, Proc. Natl. Acad. Sci. USA, 82:8701–8704 (1985) [Hoshino I].

Y. Hoshino, "Genetics Studies of Rotavirus Virulence", Summary, Third NIH Rotavirus Workshop, Bethesda, MD, 50 (1988) [Hoshino II].

A. Graham et al, J. Gen. Virol., 68:115–122 (1987).

A. Kalica et al, Virol., 112:385–390 (1981).

G. A. Losonsky et al, Pediatr. Inf. Dis., 5:25–29 (1986).

T. Vesikari et al, J. Infect. Dis., 153(5):832–839 (1986).

D. Chen et al, Proc. Natl. Acad. Sci. USA, 86:3743–3747 (1989).

O. Nakagomi et al, Mol. and Cell Probes, 3:251–261 (1989).

"WHO News and Activities", Bull WHO, 67(5):583–584 (1989).

S. Urasawa, J. Gen. Virol., 67:1551–1559 (1986).

R. Daum et al, "New Developments in Vaccines", pp. 1–57.

A. Kapikian et al, "Development of a Rotavirus (RV) Vaccine by a Jennerian and a Modified Jennerian Approach", Modern Approaches to New Vaccines, Abstract, (1987).

Spence et al, Can. J. Microbiol., 24:353–356 (1978).

T. Vesikari et al, Lancet, 2:807–811 (1983).

S. Matsuno, J. Clin. Microbiol., 5:1–4 (1977).

M. Sabara et al, J. Virol. 44:813–822 (1982).

A. Z. Kapikian et al, Infect. and Immunol., 33:415–425 (1981).

HUMAN ROTAVIRUS HCR3A AND METHOD OF GROWING SAID ROTAVIRUS

The present invention refers generally to a novel human cytopathic rotavirus and to its use as a vehicle for the expression of human rotavirus genes. More particularly, the invention involves a newly isolated human rotavirus of serotype 3 (HCR3), reassortants made from this virus, and vaccines containing the virus itself or reassortants thereof. The present invention also relates to a method for using the virus and its reassortants to express high titers of preferred human rotavirus antigens and to making vaccines using these antigens.

BACKGROUND OF THE INVENTION

Rotaviruses are the single most important etiologic agent of infectious gastroenteritis (diarrhea), which is the leading cause of infant death in the world.

Of the estimated 5 to 10 million infant deaths caused by acute infectious gastroenteritis yearly [Walsh et al, *New Engl. J. Med.*, 301:967 (1979)], rotaviruses cause between 10 and 40% of the total deaths [deZoysa and Feachem, *Bull. WHO*, 63:569 (1985)]. Rotavirus-induced infectious gastroenteritis is one of the ten leading causes of infant death, even in developed nations [Ho et al, 27th Interscience Conf. Antimicrobiol Agents Chemotherapy, p2 (1987)].

Rotaviruses of primate and bovine origin are spherical viruses, about 70 nm in diameter and characterized by a double capsid structure. The rotavirus genome has eleven segments of doublestranded RNA and an RNA polymerase. Each segment of RNA is a gene that codes for a single protein gene product. Rotavirus gene segment numbering is arbitrary, conventionally based on molecular size and electrophoretic migration.

A majority of the currently identified animal and human rotaviruses are designated as Group A rotaviruses, and share common cross-reactive antigens [Estes et al, *Immunochemistry of Viruses*, Elsevier, Amsterdam:389 (1984)]. Different species of rotaviruses are distinguishable by distinct serotype-specific virus surface antigens, which are most easily detected in conventional serum-neutralization (SN) tests. In a SN test, an antiserum prepared against a purified virus of a specific serotype scores a higher SN titer with a virus of a homologous serotype than with a virus of a heterologous serotype.

Among human rotaviruses, at least six serotypes are now recognized-serotypes 1, 2, 3, 4, 8 and 9 [Wyatt et al, *Infect. Immunol.*, 37:110 (1983); Matsuno et al, *J. Virol.*, 54:623 (1985); and Clark et al, *J. Clin. Microbiol.*, 25:1757 (1987)], with serotypes 1 through 4 causing the majority of human infections.

Currently available knowledge on the cross-immunity of various serotypes in animals and humans has provided contradictory results with regard to the necessity for serotype specific antigenic stimulation to provide immune protection against rotavirus infection. See, for example, several reports on vaccine challenge studies in animals [Wyatt et al, *Science*, 203:548 (1979); Zissis et al, *J. Infect. Dis.*, 148:1061 (1983); Sheridan et al, *J. Infect. Dis.*, 149:434 (1984)]. See, also, several reports on rotavirus vaccines evaluated in animals and humans [Mebus et al, *J. A. V. M. A.*, 163:880 (1973); Thurber et al, *Canad. Vet. J.*, 17:197 (1976); Vesikari et al, *Lancet*, 2:807 (1983); De Mol et al, *Lancet*, 2:108 (1986); Clark et al, *Amer. J. Dis. Children*, 140:350 (1986); Kapikian et al, *Vaccines*, New York, Cold Spring Harbor Lab., 357 (1985); Losonsky et al, *Pediatr. Infect. Dis.*, 5:25 (1986); and Santosham et al, 27th Int. Conf. Antimicrobiol. Agents and Chemotherapy, p. 99 (1987)].

Efforts to develop an effective rotavirus vaccine have proven disappointing to date H F. Clark, "Rotavirus Vaccines," *Vaccines*, Plotkin, S. A., Mortimer, E. A., eds. (Philadelphia, W. B. Saunders: 1988), p. 517; H F. Clark, *Immunization Monitor*, 3:3 (1989); R. S. Daum et al, "New Developments in Vaccines," Adv Pediatr Infect Dis., 6:1 (1991). See, also, "WHO News and Activities," *Bull. WHO*, 67(5): 583–587 (1989), reporting on the efficacy of rotavirus vaccines.

Animal-origin vaccines have often been unsatisfactory when evaluated in clinical trials involving orally administered living virus. For example, although the immunization of infants with bovine rotavirus vaccine strain RIT4237 has proven safe and induced measurable serum antibody response in 60–80% of recipients, early protective responses detected in trials in Finland were followed by unsuccessful clinical trials in Africa and in the United States [see, Daum et al, cited above].

Another candidate tested for use as a human vaccine, simian-origin rotavirus RRV (MMU 18006), was found to be more immunogenic than RIT4237 but also provided inconsistent protection against rotavirus disease. [G. A. Losonsky et al, *Pediatr. Infect. Dis.*, 5:25 (1986); and T. Vesikari et al, *J. Infect. Dis.*, 153:832 (1986)]. A bovine-origin rotavirus of low-tissue culture passage level, strain WC3, which is safe in infants and causes a serum antibody response in 70–95% of recipients, also provides inconsistent and limited protection.

Human rotaviruses identified to date are much more difficult to cultivate in cell culture than rotaviruses of animal origin. Human origin rotaviruses have previously been isolated successfully in cell culture using methods which were first described in K. Sato et al, *Arch. Virol.*, 69:155 (1981) and T. Urasawa et al., *Microbiol. Immunol.*, 25:1025 (1981). These methods involved inoculation of infected stool suspensions into roller tube cultures of cells of the African green monkey cell line MA104, followed by several "blind" passages of the inoculated cells. Such viruses have usually grown poorly in comparison with other species' rotaviruses; i.e., to titers 10–100 fold less than those often obtained with certain bovine and simian origin rotaviruses. Thus, in general, cell culture-adapted human rotaviruses are generally known to replicate inefficiently in vitro. This lack of an efficient means to produce larger quantities of human virus in vitro also hampers research into the virus and its antigenic components.

To date, human rotavirus isolates have been propagated only in a few cell types of simian origin. Rotaviruses of human origin have not been propagated in human diploid cell strains (HDCS). HDCS are currently considered the ideal cell substrate for production of virus vaccines for use in humans [See, e.g., M. R. Hilleman, *J. Med. Virol.*, 31:5 (1990)].

Additionally, the potential pathogenicity of human rotavirus isolates is largely unknown. In view of these above-mentioned difficulties, human rotaviruses have not been avidly pursued for vaccine use.

The failure of animal-origin vaccines to provide consistent protection and the inability to obtain readily cultivatable human rotaviruses for vaccine use have led to interest in the formation of rotavirus reassortants as potential vaccine candidates. A reassortant is formed by incorporating genes from one rotavirus coding for desired antigens (i.e., type-specific antigens) into another rotavirus. This incorporation, called "reassortment", is possible because of the segmented nature of the RNA genome of a rotavirus and its high frequency of gene reassortment during coinfection of distinct parental rotaviruses.

In rotavirus reassortants of bovine/simian origins, it was observed that the v.p.7 and v.p.4 major outer capsid proteins were independently capable of inducing a protective immune response in mice against virulent rotavirus challenge when administered at high dosages [Offit et al, *J. Virol.*, 60(2):491–496 (1986); Offit et al, *J. Virol.*, 57(2):376–378 (1986)].

Previously known reassortant rotaviruses proposed for use as human vaccine candidates involved the replacement of a single gene product encoding the v.p.7 antigen of an animal rotavirus. The 38 kd v.p.7 antigen of gene 9 or 8 of the animal virus has been replaced with the v.p.7 encoding gene of a human serotype rotavirus. U.S. Pat. No. 4,571,385 describes a method of producing a rotavirus reassortant from certain human and animal parental strains by combining the human rotavirus with a cultivatable animal rotavirus and selecting for desired reassortants with an antibody specific for the 34–38 kd glycoprotein, v.p.7 of the animal virus. [See, also, Midthun et al, *J. Virol.*, 53:949 (1985); Midthun et al, *J. Clin. Microbiol.*, 24:822 (1986).]

Compared to animal rotavirus vaccine candidates, the human/animal reassortants have been found to elicit an increased, but disappointing, incidence of human serotype-specific responses. Additionally, RRV reassortant derivatives have induced undesirable side effects, e.g., fever and gastrointestinal symptoms, in a significant proportion of vaccinees in clinical trials [Vesikari et al, cited above; and Losonsky et al, cited above].

Reassortants have been formed by co-infection of two human strains, but to date they have never been tested for vaccine use. [See, e.g., Urasawa et al., *J. Gen. Virol.*, 67:1551–1559 (1987)].

Additional difficulties encountered in inducing a vigorous and effective antibody response to rotavirus after oral administration of a potential vaccine to infants are significant interference with an active immune response in infants possessing pre-existing antibody of maternal derivation (virtually universal in very young infants) and difficulty in obtaining a universal "booster" antibody response with a second oral dose [Clark et al, Vaccine, 8:327 (1990)]. Additionally, the ability of a reassortant to induce neutralizing antisera is not itself indicative of the usefulness of the reassortant as an effective and safe vaccine for humans.

There is currently great interest in pursuing the possibility that these obstacles may be overcome by administering a killed rotavirus vaccine parenterally (e.g., by intramuscular or subcutaneous inoculation). In the case of an inoculated vaccine, it is especially important that the virus be propagated in an acceptable cell culture substrate, of which the most desirable is any human diploid cell strain. Prior to the present invention neither a human nor animal rotavirus has been reported to replicate in HDCS.

Therefore, there remains a need in the art for human origin rotavirus and reassortants thereof capable of growing to high titer in cell culture, vaccines containing these viruses or reassortants, and diagnostic and research reagents in the field of rotavirus research.

SUMMARY OF THE INVENTION

As one aspect, the present invention provides a novel newly isolated human cytopathic rotavirus, serotype 3, called HCR3. Two strains of this virus, designated HCR3A and HCR3B, are characterized by unique abilities to grow to high titer in a surprisingly broad spectrum of host cell types, including cells normally supportive of rotavirus growth and human diploid cells. Unlike other human rotaviruses, HCR3 may be isolated directly from the stool of a human infant into a suitable cell culture and observed for the production of plaques or readily visible cytopathic effect as evidence of infection. No blind passages are necessary, as for other rotaviruses.

Another aspect of the present invention is a novel method for isolating a human rotavirus comprising directly inoculating the human stool sample from a patient infected by a rotavirus, or other source of the virus, into a suitable cell culture other than MA104 and directly observing the culture for the production or plaques or readily visible cytopathic effect as evidence of infection with limited or no adaptation. In one embodiment, the method involves inoculating the sample into a diploid cell culture, such as a fetal rhesus monkey lung cell line, FRhL-2, and thereafter passaging the virus into human diploid cells.

Another aspect provided by the invention is a reassortant comprising at least one gene coding for a desired rotavirus antigen other than an antigen of HCR3, with sufficient gene segments from rotavirus strain HCR3 to confer on the reassortant the ability to grow rapidly and to high titer in cell cultures. This reassortant may also contain additional gene segments from yet another rotavirus, providing it retains the HCR3 growth abilities. In one embodiment this reassortant is characterized by at least one type-specific antigen of a human rotavirus other than HCR3. In another embodiment a reassortant is characterized by a type-specific antigen of from more than one human rotavirus other than HCR3. Any rotavirus gene determined to be of interest may also be included in a reassortant of this invention. In other embodiments, the additional rotavirus parent strain is a non-human strain, such as bovine rotavirus WC3.

Still another aspect of this invention provides a method for the high level expression of human or other animal rotavirus antigens by culturing an above-described reassortant in vitro in cells known to be acceptable for rotavirus propagation or in HDCS. The amplified antigen of interest produced by the above method may, if desired, be separated from the reassortant by conventional protein chemistry methodology.

As another aspect of this invention, there are provided diagnostic reagents which comprise human rotavirus or other species rotavirus antigens amplified as described above. Such antigens, or the reassortants themselves, may be employed as diagnostic reagents or research reagents.

As yet a further aspect of this invention there are provided vaccines for providing immunological protection against acute diarrhea caused by human rotavirus infection and methods of producing such vaccines containing attenuated HCR3 or a reassortant thereof.

Another aspect of the invention involves a method for preparing a novel reassortant virus of the invention. This method involves infecting a suitable cell substrate with a mixed infection of a rotavirus strain selected for its antigenicity, preferably a human rotavirus, and the human rotavirus HCR3 under conditions enabling gene reassortment in the infected culture and selecting for a desired reassortant. One unique embodiment of this method employs human diploid cells as the initial cell substrate. By directly plating the mixture on HDCS, a unique selective pressure is applied to enrich the mixture for production of a reassortant capable of growing well on these cells. This method may also include preparing the mixed infection in a non-human cell substrate, such as MA104 or CV-1, and thereafter passaging the virus in HDCS.

Progeny clones from plaques formed in the infected culture may be either examined by PAGE for the presence of, or subjected to other selective pressures to produce, a reassortant containing at least one selected serotype-specific antigen with sufficient human genes contributed by the HCR3 strain to confer to the reassortant its unique growth characteristics. Such a reassortant would have the potential to express large amounts of the desired human rotavirus antigens in an appropriate cell substrate for the production of virus vaccines in humans.

Another aspect of the invention provides a method of vaccinating humans against human rotavirus infection employing a HCR3 rotavirus attenuated by classical means or reassortant vaccines of the invention.

Other aspects and advantages of the present invention will be apparent upon consideration of the following detailed description of the invention, including illustrative examples of the practice thereof.

BRIEF DESCRIPTION OF THE DRAWINGS

FIG. 1 is a depiction of a photograph of a electropherotype gel on which was run the following type 3 rotavirus isolates: Bricout α, RRV, HCR3A, HCR3B, SA11, P, WI78, and Eb.

FIG. 2 is a depiction of a photograph of an electropherotype gel on which was run the reassortant HCR3A-79–9 (2 runs), parental strain reassortant WI79–9 (which is a reassortant between WC3 and the v.p. 7 gene segment of WI79), parental strain HCR3A, and grandparent strain WC3.

DETAILED DESCRIPTION OF THE INVENTION

This invention involves the isolation and characterization of a novel human rotavirus with unique growth abilities.

The novel rotavirus of human origin, HCR3 is characterized by the ability to grow at high titers on suitable cells conventionally capable of supporting the growth of rotaviruses. Suitable cells for the isolation and growth of this rotavirus to high titer include primate VERO cells (ATCC CCL-81), African green monkey kidney cells CV-1 (ATCC CCL-70); BSC-1 (ATCC CCL-26), fetal green monkey cell MA-104, and primary primate kidney cell cultures. Surprisingly, this newly isolated virus also grows to high titers in human diploid cells.

For purposes of this invention, primary primate kidney cell cultures include first, second (secondary) or third (tertiary) passages of kidney cells derived from the indicated species of primate. Human diploid cells [HDCS]are presently preferred for use in the development of human vaccines. Each of the non-human cell culture substrates may be grown in BHK medium [MacPherson, I and M. Stoker, *Virology,* 16:147 (1962)], supplemented with 10% fetal calf serum, Eagle's minimal essential medium with 10% fetal calf serum, or medium 199 with 10% fetal calf serum. HDCS are preferably grown in Eagle's minimal essential medium supplemented with 10% fetal calf serum. These media may also contain gentamicin, 25 micrograms per milliliter, if desired.

By "high titer" is meant growth at greater than $10^6$ plaque forming units (pfu) per milliliter of culture fluid. Even more desirably, the isolated virus and reassortants of this invention described in detail below are characterized by a titer of between about $10^7$ to $10^9$ pfu/ml.

Two strains of HCR3 have been isolated and identified to date. Isolate HCR3A was recovered from the stool of a human infant collected 3 days after oral administration of the bovine rotavirus vaccine WC3 (described in U. S. Pat. No. 4,636,385) during a clinical study. Isolate HCR3B was recovered from a stool collected from a normal human infant prior to the administration of a rotavirus vaccine.

Both strains have been found to be virtually indistinguishable and are assumed to be the same virus, which is postulated to be a stable virus occurring in the human population in low incidence. Hereafter, for simplicity, only HCR3A will be discussed, although HCR3B may be substituted therefor. The virus HCR3A was deposited on May 1, 1991 with the American Type Culture Collection (ATCC), 12301 Parklawn Drive, Rockville, Md., 20852 USA pursuant to regulations set out for deposits in connection with US patents. The accession number of this deposit is ATCC VR2325.

The isolation technique for isolating HCR3 is very different from and preferable to standard techniques for growing human rotaviruses. The virus strain HCR3A was isolated in a novel manner, namely by directly inoculating an infant stool suspension onto a monolayer of MA104 cells, directly observing plaques or other CPE indicative of infection, and then passaging the virus in suitable cell substrates, including human diploid cell lines (HDCS). In significant contrast to the isolation of other human rotaviruses, the virus strain HCR3A was recovered directly from an area of cytopathic effect (CPE) designated as a "plaque" appearing on the MA104 monolayer. No adaptation was necessary. The isolation of HCR3A is described in more detail in Example 1.

The plaques harvested from the above isolation were serially passaged in MA104 cells and were highly cytopathic immediately and at low passage number, e.g., passage 2 and 3) without requiring a lengthy series of blind passages characteristic of previously described human rotavirus isolates. Within less than 5 passages in MA104 cell culture, each virus produced yields of infectious virus in the range of $\geqq 10^{8.0}$ pfu/ml of fluid, a virus concentration exceeding that characteristic of other known human rotavirus strains.

Based on the results of serological analyses conducted on other type rotaviruses by PRN cross-neutralization reported in Table I, below, the isolates were named HCR3 because these rotavirus strains possess a serotype 3 surface protein v.p. 7 antigenic phenotype. As revealed by the antibody titers in Table I, the HCR3 rotaviruses are more similar antigenically to type 3 simian rotavirus SA11, than to representative known human type 3 rotaviruses, P and WI78. HCR3 has no relationship to type 1, 6 and 9 rotaviruses.

TABLE I

| | Antiserum | | | |
|---|---|---|---|---|
| Virus (type) | SA11 (3,R) | HCR3A (3,GP) | HCR3B (3,GP) | WC3 (6,GP) |
| SA11 (3) | >2,000,000 | 11,500 | 76,200 | 8,750 |
| HCR3A (3) | 1,050,000 | 88,000 | 17,200 | 135 |
| HCR3B (3) | 947,000 | 10,800 | 70,900 | <20 |
| RRV (3) | <20 | <20 | <20 | <20 |
| P (3) | 61,100 | 700 | 50 | <20 |

TABLE I-continued

| Virus (type) | Antiserum SA11 (3,R) | HCR3A (3,GP) | HCR3B (3,GP) | WC3 (6,GP) |
|---|---|---|---|---|
| WI78 (3) | 100,000 | 130 | 1045 | <20 |
| Eb (3) | 65 | <20 | 20 | 890 |
| WC3 (6) | <20 | <20 | <20 | 20,000 |
| Wa (1) | 45 | 85 | 90 | |
| WI61 (9) | <20 | <20 | <20 | |

Studies of the cell culture host range of HCR3A indicated that this virus uniquely possesses the capability of replicating to high titer without adaptation in cultures of cell types which conventionally support the in vitro growth of rotaviruses. Such cell types are listed above. In addition, HCR3A grows to high titer in the preferred human vaccine substrate system, human diploid cells (HDCS) with minimal to no adaptation. The HCR3 virus also surprisingly grows to high titer, i.e., between about $10^{6.0}$ to $10^{9.0}$, in cell cultures (including HDCS) in contrast to other human rotaviruses.

These viruses may also be identified by their characteristic electropherotype. The comparison in FIG. 1 of the electropherotypes of HCR3A and HCR3B with the other type 3 rotaviruses indicates that both strains of HCR3 are substantially identical, and differ from other known type 3 strains. For example, the monkey type 3 strains SA11 and RRV show completely different electropherotypes when compared to HCR3A and HCR3B. This is significant because SA11 and HCR3A have similar antigenic characteristics (Table I). HCR3A and B are similarly distinct from the electropherotypes of the other human type 3 strains, P, WI78 and Bricout α, and also distinct from the electropherotype of mouse strain Eb.

As shown in FIG. 2 for HCR3A, the HCR3A-79-9 reassortant described in detail in the examples below, has a different electropherotype from those of WI79-9 and WC3, based on the placement of its eleven gene segments. In comparison to HCR3A, the reassortant shows that the v.p. 7 coding gene, which appears to be either gene 7 or 8 in HCR3, is replaced by the vp7 coding gene of WI79-9, i.e. segment 9 of WI79-9, which is also segment 9 of the WI79 grandparent. This electropherotype also illustrates the bovine strain WC3 is completely different in electropherotype from HCR3.

Another unique characteristic of HCR3A includes its placement in rotavirus Subgroup 1. Subgroups are based on the identification of antigens detected without cultivating the virus, usually by radioimmunoassay or enzyme-linked immunosorbant assays. Most human rotaviruses are presently identified as belonging to Subgroup 2. Most animal rotaviruses belong in Subgroup 1.

Still another characteristic of HCR3 rotavirus strains is unusually rapid growth as indicated by single-step growth curves. Table II below shows that HCR3A after only three passages in MA104 culture was capable of replication to a titer of $10^5$ within 24 hours; and HCR3B produced similar results after only 2 passages in MA104 cells. To date the reassortant HCR3A-79-9 in MA104 cells has also been shown to be capable of replication to a similar level within 24 to 48 hours. No other known human rotavirus has been shown to be capable of replicating to that titer in an early passage.

TABLE II

| | Titers of Virus in Cell Culture Over Time | | | |
|---|---|---|---|---|
| | HCR3A Cell Type | | HCR3B Cell Type | |
| Hour | CV1 | MA104 | CV1 | MA104 |
| 0 | $1 \times 10^2$ | $3 \times 10^2$ | $1 \times 10^4$ | $2.7 \times 10^4$ |
| 2 | $2 \times 10^2$ | $5.0 \times 10^2$ | $7 \times 10^2$ | $1.3 \times 10^4$ |
| 6 | $1.0 \times 10^2$ | $4.0 \times 10^2$ | $9.0 \times 10^3$ | $2.6 \times 10^4$ |
| 12 | $3.0 \times 10^3$ | $2.0 \times 10^6$ | $3.0 \times 10^5$ | $5 \times 10^6$ |
| 24 | $2.3 \times 10^5$ | $3.1 \times 10^8$ | $2.0 \times 10^6$ | $1.8 \times 10^8$ |
| 48 | $3.0 \times 10^5$ | $1.1 \times 10^8$ | $5.4 \times 10^5$ | $6.0 \times 10^9$ |
| 72 | $2.0 \times 10^7$ | $1.0 \times 10^8$ | $3.0 \times 10^8$ | $3.8 \times 10^7$ |
| 96 | $3.0 \times 10^7$ | $1 \times 10^7$ | $5 \times 10^7$ | $2.0 \times 10^7$ |

In addition to the isolated virus free from contamination with other proteinaceous material, the invention also provides a novel direct method of propagating the virus for research and vaccine use. HCR3 may be isolated by direct inoculation onto suitable cells and isolated from plaques or other areas of CPE produced on those cells. The virus may be subsequently passaged into still other cells.

The HCR3 virus may be grown by conventional methods on cells not suitable for vaccine use, e.g., MA104 cells. The virus generated according to this method is suitable for further use as a research reagent capable of producing viral components (preferably human rotavirus components) of its or another rotavirus' genome in large quantity in culture. The virus, its reassortants, or antigens separated therefrom by conventional means may also be employed as diagnostic reagents or as agents for use as antigens in the production of antibodies.

However, the invention also provides a method for isolating and propagating virus without the need for passage or growth on MA104 cells. This method is advantageous because MA104 cells are not preferred for vaccine use. According to this method, a patient infected with a strain of HCR3 or a sample of virus obtained from another source, e.g., a depository, may be cultivated by directly inoculating the virus or tissue sample onto a selected cell type and directly observing the cells for plaques or other evidence of CPE, indicative of infection. Among desirable cell types for the direct inoculation, particularly for vaccine component use, are Vero cells, CV-1 cells, FRhL-2 cells, a fetal rhesus monkey lung cell line [R. Wallace, et al, *In Vitro*, 8:323 (1973)], or human diploid cells, such as WI38. However, other cells may also be used. After the original inoculation, the virus may be further passaged onto HDCS or a selected cell type.

As an example of the latter type of propagation of virus, a stool suspension from a patient was inoculated directly into a cell culture of FRhL-2. By the second passage, the virus titer was $7 \times 10^2$. A third passage was made in HDCS, WI38, resulting in a virus titer of $1 \times 10^3$.

The isolated virus HCR3A may be useful as a type 3 rotavirus vaccine component provided that its pathogenicity is reduced to permit safe use in human patients. One such vaccine preparation may comprise HCR3A which has been attenuated by prolonged serial passaging for a suitable number of times in a selected tissue culture to reduce the pathogenicity of the virus and permit it to be used as the effective agent in a suspension for vaccine use.

Suitable cell lines may be used alone, or in combination in serial passaging of the HCR3 strains for use as attenuated live viruses for vaccines (or in passaging the second parental rotaviruses for use in the development of reassortants, as described below). When used in combination, a separate but different cell line can be used in each of the various passages of the virus.

It is anticipated that a suitable number of passages on one or more than one type of animal cells, preferably Vero, CV-1, bovine cells or human diploid cells, is between about 50 to about 100 passages. However, additional passages may also be employed to reach an acceptable level of attenuation.

Alternatively, for use as an oral vaccine, the virus may be cultivated during prolonged passage at a low temperature, e.g., between about 25° to 30° C., in tissue culture on suitable cells. In still another embodiment, the HCR3 virus may be employed as a killed inactivated vaccine, by conventional treatment of the HCR3 virus with formalin, or another conventional inactivating agent. This inactivated or killed vaccine candidate would be suitable for use as an safe vaccine for parenteral administration.

Vaccine preparations passaged at low incubation temperatures retain the high titer characteristic of the novel virus despite numerous passages. As one example, HCR3A was passaged 14 times in MA104 cells at 30° C. retaining a titer of $2\times10^8$. In a second example, HCR3A was passaged 3 times in MRC5 cells at the same temperature, retaining a titer of $1\times10^4$. As still another example, HCR3A was passaged 6 times in MA104 cells at 25° C. to a titer of $2\times10^6$. As a final example, the virus was passaged 3 times in CV-1 cells at 30° C., retaining a titer of $3\times10^6$.

Another method for producing a vaccine component from HCR3A which is safe for administration in humans is to reassort it with another human or animal rotavirus or reassortant known to be safe and attenuated for use in humans. Another human or animal rotavirus or reassortant thereof, e.g. the attenuated bovine rotavirus WC3 or the WC3 reassortant WI79-9 described below, may be used in the generation of a reassortant vaccine. Additionally, any of the reassortants of the present invention may be inactivated for vaccine use by treatment with, e.g., formalin.

Thus another aspect of this invention is a reassortant prepared by mixed infection of HCR3A and a selected second parental rotavirus or rotavirus reassortant. The invention encompasses the construction of rotavirus reassortants, containing one or more rotaviral gene segments from one or more other selected rotaviruses, both human and animal, in place of one or more of the gene segments of HCR3. The reassortant would contain sufficient gene segments of HCR3A to enable the reassortant to grow to high titer in suitable cells.

Reassortants are made conventionally by infecting a suitable cell substrate with HCR3 (preferably attenuated for vaccine use) and a selected second rotavirus under conditions enabling gene reassortment in the infected culture. Mixed infections are designed to maximize the potential for reassortment by ensuring that large and equal concentrations of each parent virus are replicating simultaneously. After infection, sufficient time and conditions are allowed for gene reassortment. The virus is propagated in individual plaques which are induced by inoculation of the yield of the mixed infection onto another cell culture monolayer.

Such conditions include selective pressure on the mixed infection to produce reassortants in favor of the growth of the parental strains. Progeny clones may be selected from the virus yield of the mixed infection after treatment with hyperimmune antiserum to the serotype of the rotavirus contributing the antigen encoding gene [See, e.g., the method of U.S. Pat. No. 4,571,385], prior to performing plaque analysis of the population. Preferably the antiserum or a monoclonal antibody for this use is capable of binding selected antigens of the parent strains, thus preventing that parent or reassortants containing that gene segment from growing in culture.

A novel selection method which may be employed in this invention is inserting a step of cultivation in HDCS for one or more passages prior to selection of candidate plaque clones. This step enriches the reassortant mixture for progeny of various genetic composition capable of replicating in HDCS. That is, it allows selection for only reassortants which contain the HCR3 gene segments essential to growth on these cells and would also eliminate the other parent strain from growing on the culture.

Additionally, the mixed infection step may be repeated with initial reassortants and yet a third rotavirus to obtain reassortants containing at least two antigens of interest from two rotavirus other than HCR3, yet retain the growth abilities characteristic of HCR3.

Reassortant progeny clones are examined by selection of plaques of diverse morphology, e.g., by harvesting individual plaques which are then cultivated individually in cell culture or by a plaque assay of the virus yield from the mixed infection. Progeny clones from plaques formed in the infected culture are identified by running each parent and the progeny on conventional polyacrylamide gel electrophoresis with silver stain (PAGE-SS) according to the procedure of Dolan et al, *J. Clin. Microbiol.*, 21:753 (1985) for the presence of a reassortant containing gene segments from each parental strain. Since each gene segment runs at a characteristic electrophoretic mobility, the makeup of the reassortant is easily identified by comparison of the electropherotype of the reassortants with that of each parental rotavirus.

Reassortant progeny clones are selected if their PAGE-SS reveals the presence of at least one gene coding for the desired gene segments from the second (or additional) parental rotavirus. Reassortants are selected for vaccine use if their PAGE-SS reveals the presence of antigens against which immune protection is being sought, e.g., a v. p. 7 gene from a human type 1 parental strain and/or the v.p. 4 gene from a human type 2 parental strain. Performing the infections and gel electrophoresis techniques to obtain such reassortants are skills known to the art.

According to one embodiment of this invention reassortants of rotavirus HCR3 are suitable for use as expression vectors. Due to the gene segments inherited from HCR3, the reassortants would possess the capacity to produce progeny without adaptation to the cell culture, and produce such progeny at high titer. This characteristic of the reassortants is what makes HCR3 reassortants desirable to produce large quantities of any selected rotavirus antigen. For example, a reassortant of the present invention may be made to produce large quantities of other human rotavirus antigens, which are in short supply due to the difficulty in culturing the parent rotavirus. Similarly, the reassortants may be employed to produce large quantities of other animal rotavirus structural protein components or antigens, where desired.

Another valuable use for the reassortants of HCR3 relates to the ability to express large amounts of rotavirus antigen in human diploid cells with minimal or no adaptation. Because HDCS are the optimally desirable cells for vaccine generation, HCR3 reassortants of this invention may be adapted for use as vaccines, which are characterized by safety to humans and the ability to confer immune protection against human rotavirus infection. These reassortants are produced by genetic reassortment between a human HCR3 rotavirus, preferably attenuated, and a rotavirus representing an epidemiologically important human serotype, for example, a rotavirus of serotype 1, 2, 4 or 9. Preferred reassortants contain at least one gene segment from the selected rotavirus and sufficient gene segments of the rotavirus HCR3 to confer the ability to grow to high titer on a variety of suitable cell substrates, including HDCS. The pathogenic human rotavirus preferably contributes to the reassortant at least one of the major serotype-specific antigens.

Because the majority of human infections are caused by serotypes 1, 2, 3 and 4, it is desirable that the second rotavirus contribute at least the v.p.7 antigen to the reassortant. In fact, optimal coverage of the v.p.7 specificities of most natural infections may be covered by the use of several different reassortants in a vaccination therapy. The v.p.4 protein is another desirable serotype-specific antigen which is coded for by gene segment 4 of the particular human rotavirus. This gene is believed to influence host specificity to the virus.

In one desirable embodiment, a reassortant according to the present invention contains HCR3 rotavirus gene 4, encoding v.p.4, with a second human rotavirus of a preferred serotype, e.g., 1, contributing the v.p. 7 gene encoding segment (usually segment 7, 8 or 9). The second human rotavirus may also contribute the v.p.4 encoding gene to the reassortant, if desired. The remaining gene segments may be contributed solely by HCR3. Alternatively, the remaining gene segments may be from both HCR3 and the second rotavirus parent, provided that sufficient HCR3 gene segments are present to ensure similar HCR3 growth characteristics in the reassortant.

In a further desired embodiment, a reassortant is formed which contains the v.p. 7 antigen from one selected rotavirus parent of desired serotype, a v.p. 4 antigen from a second desired serotype, and sufficient gene segments from HCR3A to ensure the growth characteristics of that reassortant.

Any combination of gene segments may be reassorted with HCR3 for a reassortant with desirable vaccine characteristics, provided that the HCR3 gene segments in the ultimate reassortant are sufficient to provide the reassortant with the high titer and multi-specific host cell growth characteristics of HCR3. Thus more than one gene segment may be contributed by the more than one human rotavirus parent other than HCR3.

More than one strain may be used in the vaccination of an individual patient. Thus the second parental rotavirus may be from any selected human serotype virus. The selected human rotavirus may also be attenuated, if desired, for use in the reassortant. For use in preparing vaccine components, the rotavirus contributing the serotype-specific antigen encoding gene segment is desirably from any selected human serotype virus, although a safe animal rotavirus, such as bovine WC3 may also be used to generate reassortants for human vaccine use. In a preferred embodiment, the human rotavirus gene which encodes for the selected neutralization antigen is selected from a human rotavirus of serotype 1.

Among the human rotavirus strains particularly useful in the present invention are strains WI79 and WICC1 of serotype 1. Other serotypes may also be used in the construction of the reassortants of the present invention, for example, strain WI-SC2 of serotype 2; strains WI77, WI78, and P of serotype 3; strain WI-CC4 and Bricout β of serotype 4; and strain WI61 of serotype 9. Antigens from other newly identified human origin rotaviruses are also expected to be useful in the methods and compositions disclosed herein.

For use in producing diagnostic or research reagents or possibly animal vaccines, however, the second rotavirus parent may be selected from any animal rotavirus. Using conventional means of reassortment of diverse rotavirus strains with HCR3, any desired rotavirus protein antigens may be propagated to high titer in the suitable cell types, listed above, including HDCS.

A specific embodiment according to this invention and described below in the examples is reassortant HCR3A-79-9, containing gene segment 9 encoding v.p.7 from human rotavirus reassortant WI79-9, with gene segments 1–8, 10 and 11 from HCR3. This reassortant may be propagated in HDCS. This reassortant, as well as other reassortants encompassed by the invention, can be obtained by one skilled in the art by following the disclosure herein.

This exemplary reassortant, HCR3–79–9, was deposited with the ATCC on May 1, 1991 under accession number ATCC VR2324. The rotavirus HCR3 and its reassortants are kept permanently in the laboratory of the inventor Dr. H Fred Clark, at the Childrens Hospital of the University of Pennsylvania, Philadelphia, Pa., U.S.A. from the time they are produced. The inventor is willing to make the rotavirus and the reassortants available to appropriate persons at the USPTO upon request during the pendency of this application and will make the reassortants available to the public without restriction after issuance of a patent containing appropriate claims. Unless stated to the contrary, all deposits with the ATCC referred to herein, are available to the public upon grant of a patent to the assignee, The Wistar Institute of Anatomy and Biology, Philadelphia, Pa., USA.

As described above for vaccine components using HCR3A, the reassortants of the present invention may also be attenuated by serial passaging in more than one cell type, serial passaging at low temperatures, or inactivating with formalin or other inactivating agents. Similarly further reassortment with known safe viruses or their reassortants, e.g., WC3 or WI79-9, may also be used to produce safe vaccine components from reassortants of this invention.

Vaccines for providing immunological protection against acute diarrhea caused by human rotavirus infection may contain one or more of the novel rotavirus strains or reassortants of the present invention. For use as vaccines, the reassortant according to the invention is further characterized as capable of inducing a protective immune response in human adult and infant patients to challenge with native rotavirus without producing serious adverse effects. Optionally, the vaccines may also contain conventional vaccine adjuvants and/or carriers, e.g., aqueous suspensions of aluminum and magnesium hydroxides. The method of preparing a vaccine according to the invention involves inoculating a suitable cell substrate, e.g., HDCS cells, and passaging the virus or its reassortant therein. Because of its unique nature, HCR3 is cytopathic almost immediately, without requiring a lengthy series of passages. By combining one or more different human serotype reassortants, the vaccine can elicit a polytypic viral neutralizing antibody response.

Therefore, also included in the invention is a method of vaccinating humans against human rotavirus infection with one or more of the novel rotavirus and its reassortants. For example, a patient may be serially or simultaneously vaccinated with vaccine compositions containing reassortants carrying the desired gene segment from different human rotavirus serotypes. The vaccine preparations including one or more of the reassortants described herein are administered, preferably by oral or nasal route, at least one suitable dose. The vaccine may also be administered by injection where formalin inactivation is employed. Alternatively, the vaccine may be administered to nursing mothers as a means for transferring immunity to the infant.

The dosage for all routes of administration of a vaccine formed by the reassortant or the attenuated HCR3 virus is generally greater than $10^6$, between about $10^7$ and $10^9$ plaque forming units (pfu), with a preferred dosage being between about $10^7$ to $10^8$ pfu. Additional doses of the vaccines may also be administered at intervals of about 3 to 4 weeks. The vaccine may be administered directly to infants or to nursing mothers for purposes of transferring immunity to an infant. It may be preferable to inoculate susceptible infants and children on an annual basis prior to the "rotavirus season". Rotavirus infection in humans has been observed to occur in various geographical regions during the same season, e.g. in winter in the northeastern United States. Repeated inoculations prior to that season for susceptible infants and children may be indicated.

The preparation of a pharmaceutically acceptable vaccine, having due regard to pH, isotonicity, stability and the like, is within the skill of the art. Conventional adjuvants may also be employed in the vaccine composition, e.g., aluminum hydroxide gel. The dosage regimen involved in a method for vaccination will be determined considering various hosts and environmental factors, e.g. the age of the patient, time of administration and the geographical location and environment.

The following examples demonstrate the methods and compositions of the present invention, including a specific exemplary reassortant virus.

EXAMPLE

Isolation of the Rotaviruses

The human rotavirus strain HCR3A was recovered from the stool of a study infant [CC3-17] collected 3 days after oral administration of the bovine rotavirus vaccine WC3 (described in U. S. Pat. No. 4,636,385, which is incorporated herein by reference). Isolate HCR3B was recovered from a stool collected from study infant C4-1(29) prior to administration of rotavirus vaccine. The procedures used in the description below of the isolation of HCR3A were otherwise identical.

The stools of a single infant in a clinical trial group vaccinated with WC3 [infant WC3-17] were determined to contain rotavirus by means of plaque assay of stool. Rotavirus-containing stools were emulsified into a 5% (w/v) suspension in serum-free Eagle's Minimal Essential Medium containing 500 units of penicillin/ml, 500 micrograms of streptomycin/ml, 40 micrograms of gentamicin/ml 50 units of nystatin/ml, and 20 micrograms of trypsin/mi. The stool suspension was clarified by centrifugation at 2000× g for 30 minutes.

Clarified supernatant fluid was inoculated in a volume of 0.1 ml directly into monolayer cultures of MA104 cells on 6 well plastic plates which had previously been washed two times with PBS. After absorption of this rotavirus-containing fluid for 30 minutes at 37° C., the cultures were fed with 2.5 ml of an agarose overlay consisting of an equal mixture of 2× Eagles MEM and 1% agarose and containing 0.5 microgram/ml of purified trypsin and incubated at 37° C. in an atmosphere of 5% $CO_2$ in air. Inoculated cell cultures were stained with vital stain by, at least three days post-inoculation, adding 1.5 ml/well of overlay consisting of equal parts 2× Hanks balanced salt solution and 1% agarose, and 0.1 mg/ml neutral red stain. Plates were examined for presence of virus plaques four hours after staining and daily thereafter.

Plaques were harvested from the monolayers into 1.5 ml of Eagles MEM and were serially passaged in MA104 cells. Serial passage was accomplished by inoculating 0.2 ml of the plaque suspension onto MA104 cell stationary culture in a 24 well plate (1 $cm^2$ area/well). This passage was cytopathic; for serial passage 0.5 ml of frozen and thawed suspension was used to infect a 75 $cm^2$ flask of MA104. This highly cytopathic infection yielded $1.2 \times 10^7$ pfu/ml.

Within less than 5 passages in MA104 cell culture, the virus produced yields of infectious virus in the range of $\geq 10^{8.0}$ plaque forming units (pfu) per ml of fluid. This virus concentration exceeds that characteristic of any other human rotavirus strain (usually $10^5$ to $10^6$ pfu per ml).

EXAMPLE 2

Adaptation to HDCS

Serial passage of the virus of Example 1 was then performed in stationary cultures of HDCS cells fed with defined MCDB-104 medium supplemented with 9.375 µg/ml of unpurified trypsin [Flow Laboratory]. At varying passage levels, as appropriate, the isolated rotavirus may be genetically purified by isolation and propagation of a single plaque produced in MA104 cell culture. Mechanical aspiration of cells within a single plaque, well separated from any surrounding plaques is followed by serial propagation of virus contained in this cell suspension by standard technique.

It is presently preferred to inoculate the virus into stationary cultures of HDCS cells in the presence of serum-free medium with 0.30 µg/ml purified trypsin. The culture is harvested by freezing and thawing about 7 to 10 days after inoculation. Sub-passages are made in additional roller tubes of HDCS cells or stationary cultures of HDCS cells in tissue culture flasks.

After the initial 3 or 4 subcultures in HDCS cells, the titer of HCR3A may decline, and one enrichment passage in MA104 cells may be required. Thereafter further continuous passage in HDCS has been repeatedly obtained, e.g., to at least 15 passages to date.

The identity of the cell culture-adapted rotavirus compared with the virus in the original stool suspension is confirmed by comparison of the RNA electropherotypes induced in polyacrylamide gel. The serotype of each cell culture-adapted rotavirus may be determined by reaction with serotype-specific hyperimmune antisera to prototype rotaviruses prepared in rabbits and guinea pigs [Clark et al, (1987) supra].

EXAMPLE 3

Producing A Reassortant—HCR3A-79-9

CV1 cell culture in a 24 well plate was washed two times with PBS and individual wells were infected with serial dilutions of HCR3A [stock K333X$_2$ representing the 25th cell culture passage and 13th cell passage in HDCS] mixed with serial dilutions of the bovine-human reassortant WI79-9. WI79-9 contains 10 genes of bovine rotavirus WC3 and gene 9 which codes for the serotype-specific protein vp7 derived from the human type 1 rotavirus WI79. The WI79-9 reassortant stock was adapted to growth in CV-1 cell culture. This reassortant is described in detail in European patent application No. 323,708, published Jul. 12, 1989, which corresponds to U.S. Ser. No. 126,477, which documents are incorporated by reference herein to describe the construction of that reassortant. WI79-9 is deposited with the ATCC under accession numbers VR2194 and VR2196.

Virus was allowed to attach to the cells in a total volume of 0.2 ul per well for 30 minutes after which cells were washed two times and were fed with 1.5 ul/well of Stokers BHK medium with 13 μg/ml of unpurified trypsin. Cytopathic effect involving more than 50% of cells was apparent in most wells after 24 hours. The cells were harvested by freezing and thawing.

Each infected cell suspension was examined by PAGE (polyacrylamide gel electrophoresis) and a preparation with equal amounts of gene segments from each parent virus was selected for further study. This mixture was used to infect a 24 well plate of HDCS cells which were subsequently fed with defined medium MCDB-104 to which was added monoclonal antibody 159-T3 (obtained from Dr. Harry Greenberg, Stanford University) in a dilution of 1:60,000. The HDCS cells were used to select for gene segments corresponding to growth in HDCS. The MAb 159-T3 neutralizes virus containing a type 3 vp7. This MAb would neutralize HCR3A but not HCR3A in which the vp7 had been replaced by a serotype 1 vp7 derived from the mixed infection with WI79-9.

This infection showed greater than 75% cytopathic effect after 24 hours when it was harvested by freezing and thawing. The harvested cell suspension was inoculated in serial dilution onto MA104 cells in a standard plaque assay in which MAb 159-T3 was added to the agarose overlay at a dilution of 1:25,000. Plaques appearing in a well inoculated with the mixture diluted 1:1000 were harvested and grown out in MA104 cell culture in a 24 well plate.

These harvested plaque outgrowths were examined by PAGE. One virus population was shown to consist of a HCR3A genome with the gene 9 replaced by a gene 9 of serotype 1 rotavirus WI79. This reassortant was named HCR3A-79-9.

HCR3A-79-9 was not neutralized by MAb 159-T3 which reacts with the type 3 rotavirus vp7 or by a polyclonal antiserum to type 3 human rotavirus WI79 [Serum R213c, supplied by the inventor]that neutralized HCR3A rotavirus at a titer of 1:20,835. The acquisition of a type 1 vp7 by the reassortant was indicated by the fact that it was neutralized to a titer of 1:15,770 by a polyclonal antiserum to type 1 rotavirus which gave a similar neutralization titer against homologous type 1 rotavirus WI79 (1:9,925).

Four additional plaque-purifications were performed of HCR3A-79-9 in the absence of antiserum and nine additional passages in MA104 cell culture were performed prior to preparation of the ATCC deposit (lot FP081) of this reassortant.

HCR3A-79-9 is antigenically bivalent in VN tests with hyperimmune antisera. It reacts with antisera to human serotype 1 and serotype 3 rotaviruses. HCR3A-79-9 rotavirus replicates in HDCS cell culture. Its attenuation for orally inoculated adults and infants has not been determined. However, it may be attenuated if necessary by classical means (e.g., extended cell culture passage, low temperature passage). HCR3A-79-9 reassortant is expected to induce in a high percentage of vaccinees, a VN antibody specific for rotavirus serotype 1 and/or serotype 3.

A similar reassortant for HCR3B may be prepared by methods analogous to those above-described.

EXAMPLE 4

Method for Making Exemplary Novel Vaccines

Reassortant rotavirus HCR3A-79-9 may be prepared for vaccine use by passaging to non-pathogenicity as described above. When the reassortant is acceptably safe for human vaccine use, sterility tests consisting of inoculation of the vaccine into standard laboratory media for the culture of aerobic and anaerobic bacteria, mycobacteria, and fungi occur. The vaccine is tested for mycoplasma by inoculation of 3T3 mouse cells in culture, followed by staining with Hoechst stain for intracytoplasmic DNA. Testing for adventitious viruses include inoculation of human and primate cell cultures in the presence of serotype-specific anti-rotavirus serum obtained by conventional methods, to suppress the replication of vaccine virus, which are observed for the appearance of CPE and/or hemadsorption.

Adult and newborn mice are inoculated intracerebrally and orally with the vaccine and observed subsequently for 30 days. Adult guinea pigs are inoculated intraperitoneally and observed for 15 days post-inoculation.

The infectivity titer of the HCR3-79-9 reassortant rotavirus vaccine is determined by standard plaque assay.

EXAMPLE 5

Administration of Novel Vaccines

Administration of vaccine to adults: Adult volunteers are given a full dose ($10^7$ pfu) of HCR3A-79-9 vaccine orally after oral administration of 30 ml of Maalox to buffer stomach acids. All adults are expected to remain clinically normal. None sheds vaccine rotavirus in stool samples collected three days post infection.

Administration of vaccine to infants: HCR3A-79-9 vaccine is administered orally to infants in a volume of 2.5 ml, including 2.0 ml of vaccine and 0.5 ml of cherry syrup. Infants are given 30 ml of infant formula, or occasionally 1 ml/kg body weight of Maalox 30 minutes prior to vaccine to buffer stomach acids. In sequence, two infants are given a HCR3A-79-9 dose of $10^{4.0}$ pfu; two are given a dose of $10^{7.0}$ pfu; and 40 infants are given a dose of $10^{7.0}$ pfu. No vaccine associated symptoms of disease are expected to be observed. A number of infants given any dose of vaccine is expected to develop a virus-neutralizing serum antibody response to rotavirus serotypes 1 or 3. This immune response to a primary dose of HCR3A-79-9 is expected to be most often directed against the serotype 1, WI79, reflecting the bivalent antigenic constitution of the reassortant rotavirus.

The efficiency of induction of an immune response to HCR3A-79-9 in infants can be further enhanced by giving a second "booster" dose of vaccine orally, 30 days after the primary dose. Such a booster could consist of the HCR3A-79-9 reassortant virus used for the original inoculation or a vaccine consisting of either virus parent to the HCR3A-79-9 reassortant. Following a booster dose, antibody to serotype 3 rotavirus may be induced with a frequency similar to that obtained with serotype 1 rotavirus. Thus, antibody may be induced to the two serotypes, 1 and 3, most often responsible for rotavirus disease in infants in the United States.

Vaccine virus shed in feces is determined by plaque assay in MA104 cells of 10% stool suspension. Selected virus plaques induced by 5 day post-vaccine stool samples are harvested, propagated in MA104 cells and evaluated for vaccine virus genotype by PAGE. All serum sample pre-vaccine and post-doses 1 and 2 are titrated to endpoint for plaque-neutralizing antibody to HCR3 virus and to the rotavirus strain contributing the antigen. All sera indicating positive response to vaccine or sero-positive pre-vaccine are tested against types 1, 2, 3 and 4 rotavirus. A positive response is a 3-fold rise in serum neutralizing antibody.

Numerous modifications may be made by one skilled in the art to the methods and compositions of the present invention in view of the disclosure herein. Such modifications are believed to be encompassed in the appended claims.

What is claimed is:

1. An isolated human rotavirus strain HCR3A ATCC No. VR2325 of serotype 3, subgroup 1.

2. A method of growing the rotavirus strain HCR3A ATCC No. VR2325 comprising inoculating said rotavirus on WI38 human diploid cells in vitro and culturing said rotavirus in vitro.

* * * * *